United States Patent [19]

Commons et al.

[11] Patent Number: 5,527,794
[45] Date of Patent: Jun. 18, 1996

[54] PYRIDO[3,4-B]INDOLE DERIVATIVES AS SEROTONERGIC AGENTS

[75] Inventors: Thomas J. Commons, Wayne; Christa M. LaClair, Newtown, both of Pa.; Susan Christman, Edison, N.J.

[73] Assignee: American Home Products Corporation, Madison, N.J.

[21] Appl. No.: 448,282

[22] Filed: May 23, 1995

Related U.S. Application Data

[62] Division of Ser. No. 326,435, Oct. 20, 1994, Pat. No. 5,466,688.

[51] Int. Cl.$^6$ .................... A61K 31/445; A61K 31/55
[52] U.S. Cl. ............................... 514/212; 514/292
[58] Field of Search ........................ 514/212, 292

[56] References Cited

U.S. PATENT DOCUMENTS

| | | | |
|---|---|---|---|
| 4,336,256 | 6/1982 | Koletar et al. | 424/256 |
| 4,988,814 | 1/1991 | Abou-Gharbia et al. | 544/295 |
| 5,430,038 | 7/1995 | Martin et al. | 514/292 |

FOREIGN PATENT DOCUMENTS 9311122  6/1993  WIPO.

OTHER PUBLICATIONS

VanderMaelen et al., European Journal of Pharmacology, 129, pp. 123–130, (1986). Publication month not provided.

*Primary Examiner*—Mukund J. Shah
*Assistant Examiner*—King Lit Wong
*Attorney, Agent, or Firm*—Richard K. Jackson

[57] ABSTRACT

The compound of the formula:

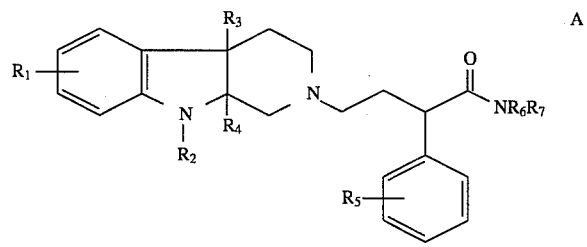

where $R_1$ and $R_5$ are independently hydrogen, fluorine, chlorine, bromine, iodine, trifluoromethyl, cyano, nitro, $CO_2H$, $C_1$–$C_6$ alkyl, $C_2$–$C_{10}$ alkenyl, $C_1$–$C_6$ alkoxy, $C_3$–$C_8$ cycloalkyl, cycloalkylalkyl, $C_3$–$C_8$ cycloalkyloxy, $C_2$–$C_7$ alkylcarbonyl, $C_2$–$C_7$ alkylcarbonyloxy, $C_2$–$C_7$ alkoxycarbonyl, mono- or di-alkylaminocarbonyl, tetrazolyl, —OH, —$(CH_2)_{1-6}$OH, —SH, —$NH_2$ or —$(CH_2)_{1-6}NR_8R_9$ where $R_8$ is hydrogen, $C_1$–$C_6$ alkyl, $C_2$–$C_7$ alkylcarbonyl, $C_2$–$C_7$ alkoxycarbonyl and $R_9$ is hydrogen or $C_1$–$C_6$ alkyl; $R_2$ is hydrogen or $C_1$–$C_6$ alkyl; $R_3$ and $R_4$ are hydrogen or taken together with the carbon atoms to which they are attached form a double bond; $R_6$ and $R_7$ are independently H, $C_1$–$C_{10}$ alkyl, $C_2$–$C_{10}$ alkenyl, $C_3$–$C_8$ cycloalkyl, cycloalkylalkyl or $R_6$ and $R_7$ taken together are polymethylene, which, with the nitrogen atom to which they are attached, form a ring of 3 to 8 atoms; or a pharmaceutically acceptable salt thereof.

1 Claim, No Drawings

PYRIDO[3,4-B]INDOLE DERIVATIVES AS SEROTONERGIC AGENTS

This is a division of application Ser. No. 08/326,435 filed Oct. 20, 1994, now U.S. Pat. No. 5,466,688.

BACKGROUND OF INVENTION

The compounds of this invention possess high affinity for the serotonin 5-HT$_{1A}$ receptor and as such are useful as antidepressant and anxiolytic agents for the treatment of a variety of central nervous system disorders such as depression, anxiety, eating disorders, sexual disfunction, addiction and related problems. As an example buspirone (U.S. Pat. No. 3,717,634) is known to display potent affinity for the 5-HT$_{1A}$ serotonin receptor. Buspirone is used extensively for the treatment of anxiety and this anxiolytic activity is believed to be due, at least partially, to its 5-HT$_{1A}$ receptor affinity [VanderMaelen et al., Eut. J. Pharmacol. 1986, 129 (123–130)].

WO 9,311,122-A and U.S. Pat. No. 4,988,814 exemplify piperazine derivatives as compounds with affinity for the 5-HT$_{1A}$ receptor.

DESCRIPTION OF THE INVENTION

This invention relates to a series of novel compounds which have activity as serotonergic agents and have the general formula A,

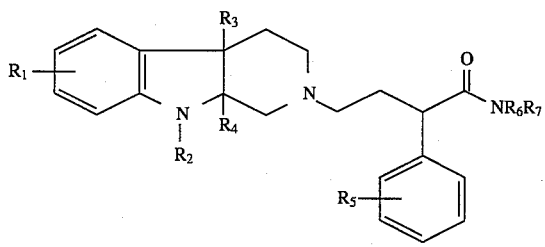

where

R$_1$ and R$_5$ are independently hydrogen, fluorine, chlorine, bromine, iodine, trifluoromethyl, cyano, nitro, CO$_2$H, C$_1$–C$_6$ alkyl, C$_2$–C$_{10}$ alkenyl, C$_1$–C$_6$ alkoxy, C$_3$–C$_8$ cycloalkyl, cycloalkylalkyl where the alkyl group is of 1 to 6 carbon atoms and the cycloalkyl group has 3 to 8 carbon atoms, C$_3$–C$_8$ cycloalkyloxy, C$_2$–C$_7$ alkylcarbonyl, C$_2$–C$_7$ alkylcarbonyloxy, C$_2$–C$_7$ alkoxycarbonyl, mono- or di-alkylaminocarbonyl in which each alkyl group, independently, contains 1 to 6 carbon atoms, tetrazolyl, —OH, —(CH$_2$)$_{1-6}$OH, —SH, —NH$_2$ or —(CH$_2$)$_{1-6}$NR$_8$R$_9$ where R$_8$ is hydrogen, C$_1$–C$_6$ alkyl, C$_2$–C$_7$ alkylcarbonyl, C$_2$–C$_7$ alkoxycarbonyl and R$_9$ is hydrogen or C$_1$–C$_6$ alkyl;

R$_2$ is hydrogen or C$_1$–C$_6$ alkyl;

R$_3$ and R$_4$ are hydrogen or taken together with the carbon atoms to which they are attached form a double bond;

R$_6$ and R$_7$ are independently H, C$_1$–C$_{10}$ alkyl, C$_2$–C$_{10}$ alkenyl, C$_3$–C$_8$ cycloalkyl, cycloalkylalkyl where the alkyl group is 1 to 6 carbon atoms and the cycloalkyl group is 3 to 8 carbon atoms or R$_6$ and R$_7$ taken together are polymethylene, which, with the nitrogen atom to which they are attached, form a ting of 3 to 8 atoms; or a pharmaceutically acceptable salt thereof.

Of these compounds, a preferred group from the viewpoint of facile production and economic considerations, are those in which R$_1$ and R$_5$, independently, represent hydrogen, fluorine, chlorine, bromine, trifluoromethyl, CO$_2$H, C$_1$–C$_3$ alkyl, C$_1$–C$_3$ alkoxy, C$_2$–C$_4$ alkoxycarbonyl, mono- or di-alkylaminocarbonyl in which each alkyl group, independently, contains 1 to 6 carbon atoms, —OH, —NH$_2$ or —(CH$_2$)$_{1-3}$NR$_8$R$_9$ where R$_8$ is hydrogen or C$_1$–C$_3$ alkyl and R$_9$ is hydrogen or C$_1$–C$_3$ alkyl; R$_2$ is H or C$_1$–C$_3$ alkyl; R$_3$ and R$_4$ are hydrogen or taken together with the carbon atoms to which they are attached form a double bond; and R$_6$ and R$_7$, taken together are polymethylene, which, with the nitrogen atom to which they are attached, form a ring of 5 to 8 atoms; or a pharmaceutically acceptable salt thereof.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids. Where the compounds of this invention contain acidic substituents such as the carboxylic acid group, salts may be formed with pharmaceutically acceptable bases to form alkali metal (such as Na, K or Li), alkaline earth metal (such as Ca or Mg), the ammonium or mono- or dialkylamine salts, the alkyl portion of said amine salts containing 1 to 6 carbon atoms.

The compounds of this invention possess one or three chiral centers depending on the identity of R$_3$ and R$_4$. Therefore they present diastereoisomers and enantiomers, which may be separated by conventional procedures. In naming the compounds throughout this disclosure and in the appended claims it is to be understood that it is intended to embrace the isomers as their mixtures and in their pure form.

The compounds of this invention are conveniently prepared by the route shown in the following scheme. Specific examples are given in the Experimental Section. These examples are for illustrative purposes only and are not to be construed as limitations for the disclosed invention. Those skilled in the art will be aware of other methods of preparing compounds of this invention. The starting materials or intermediates are available commercially or can be prepared by standard literature procedures.

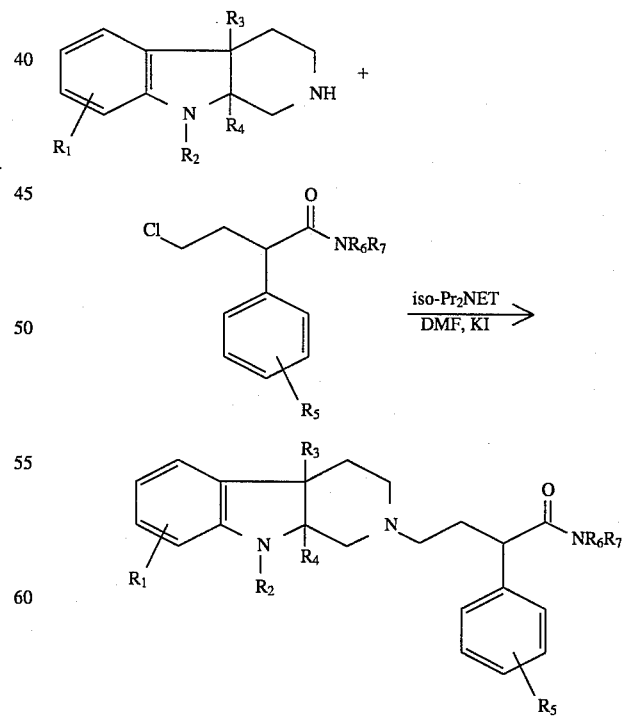

High affinity for the serotonin 5-HT$_{1A}$ receptor for the compounds of this invention was established by testing them in accordance with the standard pharmacological test procedure in which the compound's ability to displace [$^3$H]8-OHDPAT (dipropylaminotetralin) from the 5-HT$_{1A}$ serotonin receptor was determined following the procedure of Hall et al., J. Neurochem. 44 1685 (1985). This procedure is employed to analogize the properties of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity [VanderMaelen et al., Eur. J. Pharmacol. 1986, 129 (123–130)]. The results of this experimental test procedure are given in the following table:

TABLE

| | 5-HT$_{1A}$ Binding (IC$_{50}$) |
|---|---|
| Example 1 | 30.9 nM |
| Example 2 | 33.3 nM |
| Example 3 | 37.1 nM |
| Example 4 | 67.4 nM |

Hence, the compounds of this invention demonstrated high affinity for the serotonin 5-HT$_{1A}$ receptor subtype, and are therefore useful in the treatment of multi-CNS disorders amenable to treatment with antidepressant and anxiolytic agents.

Based upon this receptor binding data, the compounds of this invention are characterized as anxiolytic and/or antidepressant agents useful in the treatment of depression and in alleviating anxiety. As such, the compounds may be administered neat or with a pharmaceutical carrier to a patient in need thereof. The pharmaceutical carrier may be solid or liquid.

Applicable solid carders can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from depression or anxiety must be subjectively determined by the attending physician. The variables involved include the specific state of anxiety or depression, and the size, age and response pattern of the patient.

EXAMPLE 1

1-Azepan-1-yl-2-phenyl-4-(1,3,4,9-tetrahydro-2H-pyrido [3,4-b]indol-2 -yl]-butan-1-one A mixture of 1,2,3,4-tetrahydro-9H-pyrido[3,4-b]indole (520 mg, 3.0 mmol), 1-(azepan-1-yl)-4-chloro-2-phenyl-butan-1-one (840 mg, 3.0 mmol), N,N-diisopropylethylamine (520 μl, 3.0 mmol) and potassium iodide (500 mg, 3.0 mmol) in 15 ml of anhydrous dimethylformamide was heated under nitrogen at 80° C. for five hours. The reaction was partitioned between ethyl acetate and water. The aqueous layer was separated and the organic layer washed five times with water. The organic layer was dried (MgSO$_4$) and the solvent removed under reduced pressure to give 1.16 g of a brown oil. Purification of the oil on 200 g of silica gel (230–400 mesh) eluting with 75% ethyl acetate-hexane gave 441 mg of a solid foam. The foam was dissolved in diethyl ether containing a small amount of methylene chloride. To this solution was added 1.1 ml of 1N ethereal HCl. An oil precipitated, which after concentration of the supernatant liquid, solidified. The solid was collected by filtration and then recrystallized from isopropyl alcohol-ethanol to give 329 mg (22%) of the title compound as a light brown solid, hydrochloride, 0.375 isopropanolate, 0.375 ethanolate, mp 238°–239° C.

Elemental Analysis for C$_{27}$H$_{34}$ClN$_3$O.0.375 C$_3$H$_8$O.0.375 C$_2$H$_6$O Calc'd: C, 70.51; H, 8.04; N, 8.54 Found: C, 70.51; H, 7.86; N, 8.75

EXAMPLE 2

1-Azepan-1-yl-4-(9-methyl-1,3,4,9-tetrahydro-2H-pyrido [3,4-b]-indol-2-yl]-2 -phenyl-butan-1-one A solution of benzyl chloroformate (8.3 ml, 58 mmol) in 20 ml of anhydrous tetrahydrofuran was added dropwise under nitrogen to a warm solution of 1,2,3,4-tetrahydro-9H-pyrido[3,4 -b]indole (10.0 g, 58 mmol) and triethylamine (8.1 ml, 58 mmol) in 200 ml of anhydrous tetrahydrofuran. After the addition, the reaction was stirred at room temperature for four hours. The solvent was removed under reduced pressure and the residue partitioned between ethyl acetate and 1N HCl. The organic layer was separated, extracted one time with 1N HCl, dried (MgSO$_4$) and the solvent removed under reduced pressure to give 15.7 g of an off-white solid. Recrystallization of the solid from 100 ml of 25% hexane-ethyl acetate gave 4.23 g (24%) of the benzyloxycarbonyl derivative of the starting material as a white solid. Recrystallization of the mother liquors from ethyl acetate-diisopropyl ether gave an additional 5.84 g (33%) of material, mp 102°–104° C.

Elemental Analysis for C$_{19}$H$_{18}$N$_2$O$_2$ Calc'd: C, 74.49; H, 5.92; N, 9.14 Found: C, 74.44; H, 5.96; N, 9.30

Sodium hydride [1.5 g of a 60% oil dispersion (37 mmol)] was added in portions over fifteen minutes to a solution of the material prepared in the previous paragraph (9.5 g, 31 mmol) in 100 ml of anhydrous dimethylformamide under nitrogen at room temperature. After the addition was complete the reaction was stirred for three hours. Methyl iodide (5.8 ml, 93 retool) was then added and the reaction stirred at room temperature overnight. The reaction was quenched by the slow addition of 1N HCl. The reaction was then partitioned between 1N HCl and ethyl acetate. The organic layer was separated, extracted three times with water, dried (MgSO$_4$) and the solvent removed under reduced pressure to give 10.4 g of a light yellow solid. Recrystallization of the solid from 100 ml of 20% ethyl acetate-diisopropyl ether gave 7.59 g (76%) of the 9-methyl derivative of the starting material as a white solid, mp 100°–101° C.

Elemental Analysis for C$_{20}$H$_{20}$N$_2$O$_2$ Calc'd: C, 74.97; H, 6.29; N, 8.79 Found: C, 74.95; H, 6.30; N, 8.77

A mixture of the material prepared in the previous paragraph (4.0 g, 12 mmol) and 500 mg of 10% Pd/C in 40 ml of ethyl acetate was hydrogenated at room temperature and 40 psi for 5.5 hours. The catalyst was removed by filtration through celite and then rinsed thoroughly with ethanol and then dimethylformamide. The filtrate was concentrated under reduced pressure to give 2.39 g of an oil. The oil was dissolved in 15 ml of ethanol and 10 ml of 1N ethereal HCl was added. A solid formed which was collected by filtration, rinsed with diethyl ether, and dried under high vacuum to give 2.23 g (80%) of 1,2,3,4-tetrahydro-9-methyl-pyrido[3,4-b]indole as the hydrochloride salt, mp>250° C.

Elemental Analysis for C$_{12}$H$_{15}$ClN$_2$ Calc'd: C, 64.71; H, 6.79; N, 12.58 Found: C, 64.50; H, 6.73; N, 12.51

A mixture of the material prepared in the previous paragraph (1.56 g, 7.0 mmol), 1-(azepan-1-yl)-4-chloro-2-phenyl-butan-1-one (2.0 g, 7.0 mmol), N,N-diisopropylethylamine (2.4 ml, 14.0 mmol) and potassium iodide (1.2 g, 7.0 mmol) in 50 ml of anhydrous dimethylformamide was heated under nitrogen at 80° C. for five hours and then left at room temperature overnight. The reaction was partitioned between ethyl acetate and water. The aqueous layer was separated and the organic layer washed five times with water. The organic layer was dried (MgSO$_4$) and the solvent removed under reduced pressure to give 2.89 g of a brown foam. Purification of the foam on 400 g of silica gel (230–400 mesh) eluting with 75% ethyl acetate-hexane gave 2.34 g of an off-white foam. The foam was dissolved in diethyl ether and to this solution was added 7 ml of 1N ethereal HCl. The solid formed was collected by filtration, rinsed with diethyl ether, and dried under high vacuum to give as a light yellow solid the title compound (2.00 g, 58%) as a hydrochloride, hydrate, 0.08 diethyl etherate, mp 105°–170° C.

Elemental Analysis for C$_{28}$H$_{38}$ClN$_3$O$_2$·0.08 C$_4$H$_{10}$O Calc'd: C, 69.41; H, 7.98; N, 8.87 Found: C, 69.47; H, 7.78; N, 8.64

EXAMPLE 3

1-Azepan-1-yl-4-((trans)-9-methyl-1,3,4,4a,9,9a-hexahydro-2H-pyrido[3,4-b]indol-2-yl)-2-phenyl-butan-1-one A mixture of 1,2,3,4-tetrahydro-9-methyl-pyrido[3,4-b]indole hydrochloride, prepared in the third paragraph of Example 2 (4.50 g, 20 mmol), potassium carbonate (14.0 g, 100 mmol) and benzyl chloride (2.3 ml, 20 mmol) in 45 ml of water plus 45 ml of tetrahydrofuran was stirred at room temperature overnight. The reaction was partitioned between water and ethyl acetate. The organic layer was separated, extracted one time with saturated sodium chloride, one time with water, dried (MgSO$_4$) and the solvent removed under reduced pressure to give 4.12 g of a yellow solid. Purification of the solid on 200 g of silica gel (230–400 mesh) eluting with hexane-ethyl acetate gave 3.67 g (66%) of the 2-benzyl derivative of the starting material as a white solid, mp 109°–110° C.

Elemental Analysis for C$_{19}$H$_{20}$N$_2$ Calc'd: C, 82.57; H, 7.29; N, 10.14 Found: C, 82.29; H, 7.29; N, 10.01

A solution of 1M BH$_3$·THF (49.2 ml, 49.2 mmol) was added under nitrogen dropwise over ten minutes to a solution of the material prepared in the previous paragraph (3.63 g, 13 mmol) in 250 ml of anhydrous tetrahydrofuran at ice bath temperature. After the addition the cooling bath was removed and the reaction stirred at room temperature for thirty minutes and then refluxed for thirty minutes. After cooling to room temperature the solvent was removed under reduced pressure. To this residue 80 ml of one to one glacial acetic acid—1N HCl was added cautiously. After the evolution of gas ceased the reaction was refluxed for fifteen minutes and then stirred overnight at room temperature. The reaction was again refluxed for forty-five minutes and then cooled in an ice bath before 50% aqueous NaOH was added until the reaction was basic. The reaction was extracted with methylene chloride, dried (MgSO$_4$) and the solvent removed under reduced pressure to give 5 g of a clear oil. Purification of the oil on 600 g of silica gel (230–400 mesh) eluting with 10% ethyl acetate-hexane gave 3.70 g of a white solid. Recrystallization of the solid from diisopropyl ether gave 2.61 g (71%) of the hexahydro derivative of the starting material as a white solid, mp 59°–60° C.

Elemental Analysis for C$_{19}$H$_{22}$N$_2$ Calc'd: C, 81.97; H, 7.97; N, 10.06 Found: C, 81.84; H, 7.95; N, 10.05

A mixture of the material prepared in the preceding paragraph (2.48 g, 8.9 mmol) and 1.2 g of 10% Pd/C in 250 ml of absolute ethanol was hydrogenated at room temperature and 40 psi for 24 hours. The catalyst was removed by filtration through celite and the filtrate concentrated to dryness under reduced pressure to give 1.49 g of a tan solid. Recrystallization of the solid from diisopropyl ether gave 617 mg (37%) of the debenzylated derivative of the starting material as an off-white solid, mp 68°–70° C.

Elemental Analysis for C$_{12}$H$_{16}$N$_2$ Calc'd: C, 76.55; H, 8.57; N, 14.88 Found: C, 76.47; H, 8.68; N, 14.77

A mixture of the material produced in the previous paragraph (1.355 g, 7.2 mmol), 1-(azepan-1-yl)-4-chloro-2-phenyl-butan-1-one (2.0 g, 7.2 mmol), N,N-diisopropylethylamine (1.3 ml, 7.2 mmol) and potassium iodide (1.2 g, 7.2 mmol) in 30 ml of anhydrous dimethylformamide was heated under nitrogen at 80° C. for five hours. The reaction was partitioned between ethyl acetate and water. The organic layer was separated, washed four times with water, dried (MgSO$_4$) and the solvent removed under reduced pressure to give 2.95 g of a brown solid. Purification of the solid on 300 g of silica gel (230–400 mesh) eluting with 50% hexane-ethyl acetate gave 2.30 g of an off-white solid. Recrystallization of the solid two times from isopropyl alcohol gave 0.542 g (17%) of the title compound as a white solid. NMR analysis of this material indicated it to be a single diastereomer, mp 111°–113° C.

Elemental Analysis for $C_{28}H_{37}N_3O$

Calc'd: C, 77.92; H, 8.64; N, 9.74

Found: C, 77.52; H, 8.70; N, 9.63

The mother liquor from the above recrystallization was purified by HPLC (hexane-isopropyl alcohol) to give 169 mg of a yellow oil. The oil was dissolved in diethyl ether plus a small amount of $CH_2Cl_2$. One equivalent of 1N ethereal HCl was added and the solvent was concentrated to approximately half its volume. Diethyl ether was added and a solid formed. The solid was collected by filtration, rinsed with diethyl ether and dried under high vacuum to give 88.4 mg of a brown solid. NMR analysis indicated the solid to be the other diastereomer formed in the reaction, melting range 150°–200° C.

Elemental Analysis for $C_{28}H_{37}N_3O.HCl.4H_2O.0.1 C_4H_{10}O$ Calc'd: C, 62.30; H, 8.65; N, 7.67 Found: C, 62.81; H, 7.37; N, 7.60

EXAMPLE 4

1-Azepan-1-yl-4-((cis)-1,3,4,4a,9,9a-hexahydro-2H-pyrido[3,4-b]indol-2 -yl)-2-phenyl-butan-1-one Triethylsilane (27.8 ml, 174 mmol) was added under nitrogen to a solution of 1,2,3,4-tetrahydro-9H-pyrido [3,4-b]indole (10.0 g, 58 mmol) in 150 ml of trifluoroacetic acid and the reaction stirred at 50° C. for approximately five days. The solvent was removed under reduced pressure to give 96.88 g of a two phase oil. Purification of the oil by HPLC eluting with 2:1:1 ethyl acetate:methanol:ammonium hydroxide gave 3.83 g of the hexahydro derivative (trifluroacetic acid salt) of the starting material as a white solid, mp 146°–149° C.

Elemental Analysis for $C_{11}H_{14}N_2.CF_3CO_2H$ Calc'd: C, 54.17; H, 5.24; N, 9.72. Found: C, 54.26; H, 5.20; N, 9.70.

A mixture of the material produced in the previous paragraph (4.0 g, 14 mmol), 1-(azepan-1-yl)-4-chloro-2-phenyl-butan-1-one (3.89 g, 14 mmol), N,N-diisopropylethylamine (4.85 ml, 28 mmol) and potassium iodide (2.31 g, 14 mmol) in 250 ml of anhydrous dimethylformamide was heated under nitrogen at 75° C. for six hours. The reaction was partitioned between ethyl acetate and water. The organic layer was separated, washed multiple times with water, dried ($MgSO_4$) and the solvent removed under reduced pressure to give 5.33 g of a brown oil. Purification of the oil by HPLC eluting with methanol-methylene chloride gave 1.14 g of a yellow oil. The oil was dissolved in diethyl ether containing a small amount of methylene chloride. One equivalent of ethereal HCl was added and the solid formed was collected by filtration and dried under high vacuum to give the title compound as a light brown solid, hydrochloride, hydrate, 0.2 diethyl etherate. NMR analysis and chiral HPLC showed the material to be a mixture of diastereomers and their enantiomers, mp 105°–130° C.

Elemental Analysis for $C_{27}H_{35}N_3O.HCl.H_2O.0.2C_4H_{10}O$ Calc'd: C, 68.57; H, 8.28; N, 8.63. Found: C, 68.51; H, 8.19; N, 8.57.

EXAMPLE 5

1-Azepan-1-yl-4-((cis)-9-methyl-1,3,4,4a-hexahydro-2H-pyrido[3,4-b]indol-2 -yl)-2-phenyl-butane-1-one A solution of benzyl chloroformate (3.80 mL, 26.6 mmol) in 100 mL of anhydrous dimethyl-formamide was added under nitrogen dropwise over two hours to a solution of the material prepared in paragraph 1 of Example 4 (7.64 g, 26.6 mmol) and triethylamine (7.42, 53.2 mmol) in 100 ml of anhydrous dimethylformamide at ice bath temperature. After the addition the reaction was stirred at ice bath temperature for two hours and at room temperature overnight. The reaction was diluted with ethyl acetate, washed multiple times with water, dried ($MgSO_4$) and the solvent removed under reduced pressure to give 5.74 g of an oil. Purification of the oil on 450 g of silica gel (230–400 mesh) eluting with hexane-ethyl acetate gave 2.04 g of a solid. Recrystallization of the solid from isopropyl alcohol gave 1.44 g (18%) of the benzyloxycarbonyl derivative of the starting material, mp 88°–90° C.

Elemental Analysis for $C_{19}H_{20}N_2O_2$ Calc'd: C, 74.00; H, 6.54; N, 9.08 Found: C, 73.96; H, 6.54; N, 9.03

Sodium hydride (271 mg of a 60% oil dispersion containing 6.78 mmol) was added in portions under nitrogen to a solution of the material prepared in the preceding paragraph (1.74 g, 5.65 mmol) in 20 ml anhydrous dimethylformamide at room temperature. After the addition, the reaction was stirred a room temperature for two hours. Methyl iodide (1.06 ml, 16.95 mmol) was added and the reaction stirred at room temperature overnight. The reaction was diluted with ethyl acetate, washed multiple times with water, dried ($MgSO_4$) and the solvent removed under reduced pressure to give 1.0 g of an oil. Purification of the oil on 450 g of silica gel (230–400 mesh) eluting with hexane-ethyl acetate gave 850 mg (47%) of the methyl derivative of the starting material as a clear oil, MS m/e 322 [M$^+$].

Elemental Analysis for $C_{20}H_{22}N_2O_2$ Calc'd: C, 74.51; H, 6.88; N, 8.69 Found: C, 73.35; H, 6.85; N, 8.52

A mixture of the material prepared in the preceding paragraph (800 mg, 2.48 mmol) and 120 mg of 10% Pd/C in 80 ml of ethanol was hydrogenated at room temperature and 40 psi for 17 hours. The catalyst was removed by filtration through celite and the solvent was removed under reduced pressure to give 426 mg (91%) of a brown oil which was used in the next step without purification.

A mixture of the material prepared in the preceding paragraph (382 mg, 2.03 mmol), 1-azepan-1-yl)-4-chloro-2-phenyl-butan-1-one (568 mg, 2.03 mmol), N,N-diisopropylethylamine (353 μl, 2.03 mmol)and potassium iodide (337 mg, 2.03 mmol) in 15 ml of anhydrous dimethylformamide was stirred under nitrogen at 80° C. for five hours. The reaction was partitioned between ethyl acetate and water. The aqueous layer was separated and the organic layer washed multiple times with water. The organic layer was dried ($MgSO_4$) and the solvent removed under reduced pressure to give 739 mg of a brown oil. Purification of the oil on 200 g of silica gel (230–400 mesh) eluting with ethyl acetate-methylene chloride gave 361 mg of an off-white solid. This solid was further purified by trituration with hexane to give 205 mg of a solid. The solid (195 mg, 0.45 mmol) was dissolved in diethyl ether and 452 μl (0.45 mmol) of 1N ethereal HCl was added. The solid formed was collected by filtration and dried under high vacuum to give as an off-white solid the title compound (120 mg, 12%) as a hydrochloride, sesquihydrate, 0.2 diethyl etherate, MS, m/e 431 (M$^+$-HCl).

Elemental Analyses for $C_{28}H_{37}N_3O\cdot HCl\cdot 1.5 H_2O\cdot 0.2C_4H_{10}O$ Calc'd: C, 67.84; H, 8.30; N, 8.24 Found: C, 68.09; H, 8.43; N, 8.48

What is claimed is:

1. A method for relieving the symptoms of anxiety which comprises administering to a mammal in need thereof, orally or parenterally, a compound of the formula:

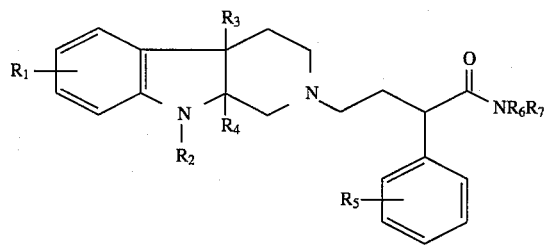

where $R_1$ and $R_5$ are independently hydrogen, fluorine, chlorine, bromine, iodine, trifluoromethyl, cyano, nitro, $CO_2H$, $C_1$–$C_6$ alkyl, $C_2$–$C_{10}$ alkenyl, $C_1$–$C_6$ alkoxy, $C_3$–$C_8$ cycloalkyl, cycloalkylalkyl where the alkyl group is of 1 to 6 carbon atoms and the cycloalkyl group has 3 to 8 carbon atoms, $C_3$–$C_8$ cycloalkyloxy, $C_2$–$C_7$ alkylcarbonyl, $C_2$–$C_7$ alkylcarbonyloxy, $C_2$–$C_7$ alkoxycarbonyl, mono- or di-alkylaminocarbonyl in which each alkyl group, independently, contains 1 to 6 carbon atoms, tetrazolyl, —OH, —$(CH_2)_{1-6}$OH, —SH, —$NH_2$ or —$(CH_2)_{1-6}NR_8R_9$ where $R_8$ is hydrogen, $C_1$–$C_6$ alkyl, $C_2$–$C_7$ alkylcarbonyl, $C_2$–$C_7$ alkoxycarbonyl and $R_9$ is hydrogen or $C_1$–$C_6$ alkyl;

$R_2$ is hydrogen or $C_1$–$C_6$ alkyl;

$R_3$ and $R_4$ are hydrogen or taken together with the carbon atoms to which they are attached form a double bond;

$R_6$ and $R_7$ are independently H, $C_1$–$C_{10}$alkyl, $C_2$–$C_{10}$alkenyl, $C_3$–$C_8$ cycloalkyl, cycloalkylalkyl where the alkyl group is 1 to 6 carbon atoms and the cycloalkyl group is 3 to 8 carbon atoms or $R_6$ and $R_7$ taken together are polymethylene, which, with the nitrogen atom to which they are attached, form a ring of 3 to 8 atoms; or a pharmaceutically acceptable salt thereof, in an anxiolytic amount.

* * * * *